United States Patent [19]

Renet

[11] 4,045,300

[45] Aug. 30, 1977

[54] METHOD FOR REDUCING THE RESPONSE TIME IN OXYGEN MEASURING PROBES

[75] Inventor: Claude Renet, Pontchartrain, France

[73] Assignee: "Meci" Materiel Electrique de Controle et Industriel, Paris, France

[21] Appl. No.: 573,720

[22] Filed: May 1, 1975

[30] Foreign Application Priority Data

May 6, 1974 France ............................... 74.15550

[51] Int. Cl.² ........................................... G01N 27/46
[52] U.S. Cl. .................................. 204/1 T; 204/195 S
[58] Field of Search ........................... 204/1 S, 195 S; 136/86 F

[56] References Cited

U.S. PATENT DOCUMENTS

| 3,400,054 | 9/1968 | Ruka et al. | 204/1 S |
| 3,773,641 | 11/1973 | Fitterer | 204/195 S |

*Primary Examiner*—T. Tung
*Attorney, Agent, or Firm*—Pollock, Vande Sande & Priddy

[57] ABSTRACT

A method for reducing the response time in the measurement of the oxygen content in molten metals by means of a probe of the type comprising a solid electrolyte which produces an electromotive force depending on the ratio of the partial pressure of oxygen in the molten metal to the partial pressure of oxygen in a reference medium contained in the probe, said method comprising producing a temperature rise of the probe thereby to accelerate the establishment of thermal equilibrium with the molten metal.

14 Claims, No Drawings

METHOD FOR REDUCING THE RESPONSE TIME IN OXYGEN MEASURING PROBES

The invention relates to a method and apparatus for reducing the response time of a consumable probe for measuring the oxygen in molten metals.

One important application of the present invention is measuring the oxygen in molten steel and the invention will be described essentially with reference to this application, it being understood that the scope of the invention extends to other metals, such as for example copper alloys, tin alloys etc.

A method for measuring dissolved oxygen in a high temperature metal bath consists of immersing in this bath, for a short period of time, a consumable probe comprising a solid electrolyte which produces an electromotive force depending on the ratio of the partial oxygen pressure existing in the bath to the partial oxygen pressure existing in a reference medium contained in the probe.

This reference medium is generally constituted by the powdered mixture of a metal and its lowest oxide. In fact, a balanced mixture of this type produces a very stable partial oxygen pressure at a given temperature.

The response time of the probe, i.e. the period which elapses between the time of introducing the probe into the bath and the time when the electromotive force produced by the probe is effectively representative of the partial oxygen pressure, is determined by the conditions under which the solid electrolyte and reference medium are heated and brought into thermal equilibrium with the bath.

The electromotive force of the probe is transmitted to a measuring and recording device by leads which pass into a hollow rod at the end of which the probe is mounted. The part of the rod which is immersed in the bath must be provided with sufficient thermal protection in order to prevent deterioration of the rod and leads during the measurement.

This thermal protection is expensive and it is advantageous to achieve conditions which make it possible to carry out the measurements as quickly as possible in order to reduce the cost of the thermal protection, since the latter is directly connected to the duration of protection required.

Now, under predetermined conditions of use, the response time depends solely on the geometry and technology of the probe. When the latter are fixed, the response time is also fixed.

It thus seems that a limit is reached, below which it is very difficult to reduce the response time.

It is precisely the object of the present invention to reduce the response time.

This is achieved, according to the invention, by producing within the reference medium, a rise in temperature which accelerates the establishment of thermal equilibrium with the bath.

This rise in temperature may be achieved by any appropriate means capable of causing a liberation of heat and which is initiated from outside the bath or by the bath itself.

An exothermic chemical reaction initiated within the reference medium by heating due to the introduction of the probe into the bath and chosen so as not to disturb the operation of the probe is preferred.

This chemical reaction will generally be a redox reaction wherein the final products do not substantially modify the partial pressure of oxygen produced by the reference medium.

If M designates the metal of the reference medium, there is added to this metal, according to the present invention:

a. a metal A having a greater affinity for oxygen than M and/or
b. an oxide of a metal B having a lesser affinity for oxygen than M.

The choice between the combination $a\ b$ or $a + b$ could be guided by the following considerations:

If the metal M is slightly or moderately oxidisable (ex: Cu-Ni-Mo) the solution $a$ is preferred. Apart from metals which have very great affinity for oxygen such as Zr, Al, Mg (but are dangerous to handle), it is possible to use metals having a slightly less affinity such as Cr or Mn as the metal A.

If the metal M has quite a great affinity for oxygen (ex: Cr) the solution $a$ would be possible solely with metals which are dangerous to handle in the powdered state and thus the combination $b$ would be preferred, the metal B being chosen from substances such as Co, Ni, Mo, whose lower oxides have low fusibility.

In most cases, the combination $a + b$ is theoretically possible, but there is a risk of technological difficulties (dealing with pyrotechnic powders) or practical difficulties (liquefaction of the mixture, formation of eutectics with the electrodes ...). It should therefore be used with precautions.

In addition, it is necessary to be cautious with certain mixtures, whereof one or more constituents would be liquid at the temperature of use. Thus, above 1,100° C, Cu and CuO are liquid and miscible. Other constituents may also be soluble in the copper. Due to the change in the number of phases present, there is a risk of altering the conditions of equilibrium and of not achieving the desired result. It is thus prudent to be limited to combinations of substances which, after having reacted, give solely solid products at the operating temperature, which is the case for mixtures of $MoO_2$ or $Cr_2O_3$ with Al, Zr, Mg, Ti, etc.

For carrying out the method of the invention by a redox reaction, in particular in the case of molten steel baths, preference is given to the following possibilities:

The reference medium is a powder which contains a metal and/or its lowest oxide and one incorporates in this powder a metal having a greater affinity for oxygen and the metals used are chosen from the group constituted by: Ni, Co, Mo, Cr, Mn, Ta, V, Si, Ti, Mg, Al, Zr, these metals being arranged in increasing order of their affinity for oxygen, the metal of the reference medium being chosen from the first four and the metal added being any of following the reference metal in the list.

The reference medium is a powder which contains a metal and optionally its lowest oxide and one adds to this powder an oxide of a metal having a lesser affinity for oxygen than the metal of the reference medium and the metals used are chosen from the group constituted by: Fe, Cu, Ni, Co, Mo, Cr, these metals being arranged in increasing order of their affinity for oxygen, the metal of the reference medium being chosen from the last four and the oxide being an oxide of one of the metals preceding the reference metal in the list.

The reference medium is a powder containing a metal and its lowest oxide, one incorporates in this powder a metal having a great affinity for oxygen and an oxide of a metal having a lesser affinity for oxygen than the former and the various metals used are chosen from metals of the group: Fe, Cu, Ni, Co, Mo, Cr, Mn, Ta, B, Si, Ti, Mg, Al, Zr, these metals being arranged in increasing order of their affinity for oxygen, the metal of the reference medium being chosen from the group: Ni, Co, Mo, Cr, the metal having an affinity for oxygen being one of the metals which follows the reference metal in the above list and the oxide being an oxide of a metal which precedes the reference metal in said list.

As an example, we will consider hereafter the case of a reference medium whereof the metal is molybdenum, it being understood that the arguments may be transferred to other cases, in particular nickel and chromium.

To cause an exothermic redox reaction within the mixture Mo, $MoO_2$, it is possible to use either a reducing agent or an oxidising agent.

Example 1

Addition of a highly reducing metal to the reference medium.

This metal may be Zr or Al, possibly Cr in the case of NiO or $MoO_2$. Reactions of the following type occur:

$$Zr + 2 MoO_3 \rightarrow ZrO_2 + 2 MoO_2$$

or $$Zr + 2 MoO_2 \rightarrow ZrO_2 + MoO_2 + Mo$$

If the oxide exists in sufficient quantity in order that all the zirconium is oxidised, in practice, the final partial oxygen pressure will not depend on that of $ZrO_2$ which is very low, but will be very close to that of $MoO_2$. Thus, the same final result will be obtained as without the zirconium, but with a liberation of heat accelerating the rise in temperature of the reference medium. The magnitude of heating could be modified by measuring the proportion of reagent in the mixture:

$$x Zr + y MoO_2 + z Mo \rightarrow x ZrO_2 + (y-x)$$
$$MoO_2 + (z+x) Mo$$

To determine $x$, $y$, $z$, it is sufficient to calculate from thermodynamic data, the temperature rise obtained for the total mass by the energy liberated by the reaction. An indetermination remains regarding one of the parameters, which is removed by giving this parameter a sufficient value to ensure good electric conductivity of the mixture.

$MoO_3$ could be used as the oxide, but in consideration of the vaporisation of the substance above 1,000° C, then there is a possibility of an excessive increase in pressure if this vaporisation occurs before the end of oxidation of the zirconium and for this reason $MoO_2$ is preferred.

One could also consider replacing zirconium by aluminium, but owing to the fact that this element melts at low temperatures, separation of the mixture as well as rupture of the casing containing the reference medium during the re-solidification to form alumina are to be feared.

Nevertheless, the use of aluminium is not excluded in certain cases.

Numerical Application

Let us consider the reaction:

$$x Zr + y MoO_2 + z Mo = x ZrO_2 + (y - x) MoO_2 + (z + x) Mo.$$

$x$, $y$ and $z$ representing molar numbers, the total mass is:

$$M = 91 x + 128 y + 96 z$$

if we take an average mass heat of 0.2cal/g, the calorific capacity is 0.2 $x$ Mcal/° C.

Since the free heat content on the formation of $ZrO_2$ is —180,000 calories at 1,600° C, and the free heat content on the formation of $MoO_2$ is —65,000 calories at 1,600° C, the heat liberated will be $(180,000-65,000)x$ and the heating:

$$\Delta T = 115,000\ x/0.2M$$

If it is desired that $\Delta I = 1000°$ C, for M = 0.6g, one obtains:

$$x = (0.2 \times 0.6 \times 1,000)/115,000 = 1.04 \cdot 10^{-3}\ \text{mole}$$

or: 0.95g or: 15.8% of Zr.

It remains to determine $y$ and $z$. If, arbitrarily, $z = 2y$ to ensure good electronic conductivity of the mixture, one obtains:

$$(128 + 2 \times 96)y = 320\ y = 0.505g$$

$$y = 1.58 \cdot 10^{-3}\ \text{or 0.202g or 33.7\% of } MoO_2$$

whence:

$$z = 3.16 \cdot 10^{-3}\ \text{or 0.303g or 50.5\% of Mo.}$$

Example II

Addition of an oxidising agent to the metal of the reference medium

Consider the reaction:

$$2\ Cu\ O + Mo \rightarrow 2\ Cu + MoO_2$$

If Mo is in excess and since $MoO_2$ is much more stable than CuO, this oxide will be entirely reduced and the partial oxygen pressure obtained at equilibrium will be that of $MoO_2$.

Copper oxide could be replaced by silver oxide as the oxidising agent, but with these two substances, there is a risk of being hindered by the low melting points of the metals and oxides. The addition of an oxidising agent thus seems to be better suited to chromium than to molybdenum. In fact, since in this case the reaction is stronger, a smaller quantity of reagent is required and if the latter is liquefied, it may be retained by capillarity in the excess solid powder.

Numerical Application

In this case, since the presence of $MoO_2$ is not essential at the beginning, we may consider the reaction:

$$2 \times CuO + y Mo \rightarrow 2 \times Cu + x MoO_2 + (y - x) Mo$$

The mass equation is:

$$159 x + 96 y = M$$

The liberation of heat is due essentially to the formation of $MoO_2$, whereof the free heat content is approximately —65,000 calories at 1,600° C, that of CuO being close to zero at the same temperature. The heating $\Delta T$ will thus be such that:

$$65{,}000 \; x = 0.2 \times M \times \Delta T$$

If we take $\Delta T = 1{,}000°$ C and $M = 0.6$g, then:

$2x = 3.7 \cdot 10^{-3}$ mole $= 0.294$g $= 49\%$ of CuO $y = 3.19 \cdot 10^{-3}$ mole $= 0.306$g $= 51\%$ of Mo

Example III

Addition of an oxidising agent and a reducing agent to the reference medium

It is possible to envisage a combination of the two preceding methods, for example:

$$Zr + 2\,CuO \rightarrow ZrO_2 + 2\,Cu$$

In this case, it is ensured that there is sufficient oxidising agent to thoroughly oxidise the zirconium and sufficient reducing agent to reduce all the Cu, whence:

$$Zr + (2+x)\,CuO + y\,Mo \rightarrow ZrO_2 + (2+x)\,Cu + x/2\,MoO_2 + (y - x/2)\,MO$$

Numerical Application $x = 1$ is fixed arbitrarily to ensure the necessary excess oxidising agent. The reaction becomes:

$$Zr + 3\,CuO + y\,Mo \rightarrow ZrO_2 + 3\,Cu + 1/2\,MoO_2 + (y - 1/2)\,Mo$$

for 1 mole of Zr, the reaction liberates:

$180{,}000 + 65{,}000/2 = 212{,}500$ calories.

whence for $\Delta T = 1{,}000$ and $c = 0.2$:

$$Mc\,\Delta T = 200(91 + 238.5 + 96\,y) = 212{,}500$$

whence: $M = 1{,}062.5$ and $96\,y = 733$
proportion of Zr: $91/1{,}062 = 8.6\%$
proportion of CuO: $238.5/1{,}062 = 22.4\%$
proportion of Mo: $733/1{,}062 = 69\%$.

The advantage of this reaction is using a large excess of molybdenum which does not react. It is thus easy to vary $\Delta T$ by modifying the proportion of Mo in the mixture.

The method of the invention may be carried out without any appreciable modification in the apparatus normally used for measuring oxygen in molten metals. In fact, when a redox reaction is used for producing the rise in temperature in a powdered reference medium, it is sufficient to add to this powder the metal or oxide which has been chosen depending on the constituents of the reference medium to obtain the exothermic chemical reaction, which is initiated by the simple introduction of the probe into the bath.

What is claimed is:

1. A method for reducing the response time in the measurement of the oxygen content in molten metal by means of a probe of the type comprising a solid electrolyte which produces an electromotive force depending on the ratio of the partial pressure of oxygen in the molten metal to the partial pressure of oxygen in a powdered reference medium contained in the probe, said method comprising producing a temperature rise of the probe by an exothermic oxidation-reduction chemical reaction initiated in the powdered reference medium and by the bath itself and whereof the final products of said reaction do not substantially modify the partial pressure of oxygen produced by the reference medium to thereby accelerate the establishment of thermal equilibrium with the molten metal, wherein the reference medium is a powder which contains a metal and optionally its lowest oxide and wherein added to this powder is an oxide of a metal having a lower affinity for oxygen than the metal of the reference medium in an amount so that the final products do not substantially modify the partial pressure of oxygen produced by the reference medium, and wherein the metals used are chosen from the group constituted by: Fe, Cu, Ni, Co, Mo, Cr, these metals being arranged in increasing order of their affinity for oxygen, the metal of the reference medium being chosen from the last four and the oxide being an oxide of any one of the metals preceding the reference metal in the list.

2. The method of claim 1 wherein the metal of the reference medium is Mo and the oxide is CuO.

3. A method for reducing the response time in the measurement of the oxygen content in molten metal by means of a probe of the type comprising a solid electrolyte which produces an electromotive force depending on the ratio of the partial pressure of oxygen in the molten metal to the partial pressure of oxygen in a powdered reference medium contained in the probe, said method comprising producing a temperature rise of the probe by an exothermic oxidation-reduction chemical reaction initiated in the powdered reference medium and by the bath itself and whereof the final products of said reaction do not substantially modify the partial pressure of oxygen produced by the reference medium to thereby accelerate the establishment of thermal equilibrium with the molten metal, wherein the reference medium is a powder containing a metal and its lowest oxide, wherein there is incorporated in this powder a metal having a higher affinity for oxygen and an oxide of a metal having a lower affinity for oxygen than the metal of the reference medium.

4. Method according to claim 3, wherein the various metals used are chosen from the metals of the group: Fe, Cu, Ni, Co, Mo, Cr, Mn, Ta, V, Si, Ti, Mg, Al, Zr, these metals being arranged in increasing order of their affinity for oxygen, the metal of the reference medium being chosen from the group: Ni, Co, Mo, Cr, the metal having a higher affinity for oxygen being one of the metals which follows the reference metal in the above list and the oxide being an oxide of a metal which precedes the reference metal in said list.

5. The method of claim 4 wherein said metal of the reference medium is Mo, the metal having a higher affinity for oxygen is Zr, and said oxide of a metal being CuO.

6. A method for reducing the response time in the measurement of the oxygen content in molten metal by means of a probe of the type comprising a solid electrolyte which produces an electromotive force depending on the ratio of the partial pressure of oxygen in the molten metal to the partial pressure of oxygen in a powdered reference medium contained in the probe, said method comprising producing a temperature rise of the probe by an exothermic oxidation-reduction chemical reaction initiated in the powdered reference medium and by the bath itself and whereof the final products of said reaction do not substantially modify the partial pressure of oxygen produced by the reference medium to thereby accelerate the establishment of thermal equilibrium with the molten metal, wherein the reference medium is a powder which contains a metal and/or its lowest oxide and wherein added to this metal is a metal having a greater affinity for oxygen in an amount so that the final products do not substantially modify the partial pressure of oxygen produced by the reference medium and wherein the metal of the reference medium is Ni or Mo and the added metal is Zr or Al.

7. The method of claim 6 wherein the metal of the reference medium is Mo and the added metal is Zr.

8. Apparatus for reducing the response time in the measurement of the oxygen content of molten metals comprising a probe which comprises a solid electrolyte adapted to produce an electromotive force depending on the partial pressure of oxygen in a molten metal and the partial pressure of oxygen in a powdered reference media in the probe and a metal or metal oxide in the reference media capable of reacting at the time of introduction of the probe into molten metal thereby to cause an exothermic oxidation-reduction chemical reaction producing a temperature rise which accelerates establishment of thermal equilibrium with the bath, and whereby the final products of said reaction do not substantially modify the partial pressure of oxygen produced by the reference medium, wherein the reference medium is a powder which contains a metal and optionally its lowest oxide and wherein added to this powder is an oxide of a metal having a lower affinity for oxygen than the metal of the reference medium in an amount so that the final products do not substantially modify the partial pressure of oxygen produced by the reference medium and wherein the metals used are chosen from the group constituted by: Fe, Cu, Ni, Co, Mo, Cr, these metals being arranged in increasing order of their affinity for oxygen, the metal of the reference medium being chosen from the last four and the oxide being an oxide of any one of the metals preceding the reference metal in the list.

9. The apparatus of claim 8 wherein the metal of the reference medium is Mo and the oxide is CuO.

10. Apparatus for reducing the response time in the measurement of the oxygen content of molten metals comprising a probe which comprises a solid electrolyte adapted to produce an electromotive force depending on the partial pressure of oxygen in a molten metal and the partial pressure of oxygen in a powdered reference media in the probe and a metal or metal oxide in the reference media capable of reacting at the time of introduction of the probe into molten metal thereby to cause an exothermic oxidation-reduction chemical reaction producing a temperature rise which accelerates establishment of thermal equilibrium with the bath, and whereby the final products of said reaction do not substantially modify the partial pressure of oxygen produced by the reference medium, wherein the reference medium is a powder containing a metal and its lowest oxide, wherein there is incorporated in this powder a metal having a higher affinity for oxygen and an oxide of a metal having a lower affinity for oxygen than the metal of the reference medium.

11. The apparatus of claim 10 wherein the various metals used are chosen from the metals of the group: Fe, Cu, Ni, Co, Mo, Cr, Mn, Ta, V, Si, Ti, Mg, Al, Zr, these metals being arranged in increasing order of their affinity for oxygen, the metal of the reference medium being chosen from the group: Ni, Co, Mo, Cr, the metal having a higher affinity for oxygen being one of the metals which follows the reference metal in the above list and the oxide being an oxide of a metal which precedes the reference metal in said list.

12. The apparatus of claim 11 wherein said metal of the reference medium is Mo, the metal having a higher affinity for oxygen is Zr, and said oxide of a metal being CuO.

13. Apparatus for reducing the response time in the measurement of the oxygen content of molten metals comprising a probe which comprises a solid electrolyte adapted to produce an electromotive force depending on the partial pressure of oxygen in a molten metal and the partial pressure of oxygen in a powdered reference media in the probe and a metal or metal oxide in the reference media capable of reacting at the time of introduction of the probe into molten metal thereby to cause an exothermic oxidation-reduction chemical reaction producing a temperature rise which accelerates establishment of thermal equilibrium with the bath, and whereby the final products of said reaction do not substantially modify the partial pressure of oxygen produced by the reference medium, wherein the reference medium is a powder which contains a metal and/or its lowest oxide and wherein added to this metal is a metal having a greater affinity for oxygen in an amount so that the final products do not substantially modify the partial pressure of oxygen produced by the reference medium and wherein the metal of the reference medium is Ni or Mo and the added metal is Zr or Al.

14. The apparatus of claim 13 wherein the metal of the reference medium is Mo and the added metal is Zr.

* * * * *